(12) United States Patent
Kuo et al.

(10) Patent No.: US 7,767,707 B2
(45) Date of Patent: Aug. 3, 2010

(54) FUSED PYRAZOLYL COMPOUNDS HAVING AN AMINOALKYLCARBONYL GROUP

(75) Inventors: Sheng-Chu Kuo, Taichung (TW); Che-Ming Teng, Taipei (TW); Fang-Yu Lee, Taichung (TW)

(73) Assignee: Yung Shin Pharm. Ind. Co., Ltd., Taichung (TW)

( * ) Notice: Subject to any disclaimer, the term of this patent is extended or adjusted under 35 U.S.C. 154(b) by 127 days.

(21) Appl. No.: 12/292,160

(22) Filed: Nov. 13, 2008

(65) Prior Publication Data

US 2009/0131681 A1    May 21, 2009

Related U.S. Application Data

(60) Provisional application No. 60/996,515, filed on Nov. 21, 2007.

(51) Int. Cl.
 *A61K 31/416* (2006.01)
 *C07D 231/56* (2006.01)

(52) U.S. Cl. .................. 514/406; 548/361.1

(58) Field of Classification Search .......... 514/406; 548/361.1
 See application file for complete search history.

(56) References Cited

U.S. PATENT DOCUMENTS 7,378,532 B2 * 5/2008 Kuo et al. .............. 548/361.1

\* cited by examiner

Primary Examiner—Kamal A Saeed
Assistant Examiner—Samantha L Shterengarts
(74) Attorney, Agent, or Firm—Bacon & Thomas, PLLC

(57) ABSTRACT

A fused pyrazolyl compound having an anti-tumor potency of the following formula is synthesized:

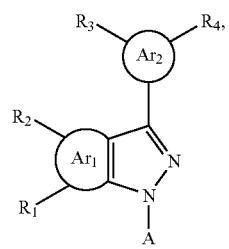

wherein A is

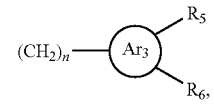

in which n is 0, 1, 2, or 3; $Ar_1$ is benzene, thiophene or furan; $Ar_2$ is furyl; and $Ar_3$ is phenyl; $R_1$ and $R_2$ independently are hydrogen, halogen or $-(CH_2)_mOR^e$; $R_3$ is hydrogen or alkyl; $R_4$ is $-(CH_2)_r-A_1$, wherein r is an integer of 1-5, and $A_1$ has a formula of $-O-C(O)-(CR^cH)_q-NR^{c'}R^{d'}$; $R_5$ and $R_6$ independently are hydrogen, halogen, or alkyl, or $R_5$ and $R_6$ together are $-O(CH_2)_mO-$; $R^c$ is H, halogen, nitro, cyano, alkyl, or aryl; $R^e$ is H, alkyl, or aryl; $R^{c'}$ and $R^{d'}$ independently are H, alkyl, or aryl; m is 0, 1, 2, 3, 4, 5, or 6; and q is 1, 2, 3, 4, 5, or 6; or a salt thereof.

22 Claims, No Drawings

FUSED PYRAZOLYL COMPOUNDS HAVING AN AMINOALKYLCARBONYL GROUP

CROSS-REFERENCE TO RELATED APPLICATION

This patent application claims the benefit under 35 USC 119(e) of U.S. Provisional Patent Application No. 60/996,515, filed Nov. 21, 2007.

FIELD OF THE INVENTION

This invention is related to novel fused pyrazolyl compounds, and the use thereof in inhibiting cancer cell growth.

BACKGROUND OF THE INVENTION

U.S. Pat. No. 7,378,532 B2 discloses novel fused pyrazolyl compounds, and the use thereof in inhibiting cancer cell growth, details of which are incorporated herein by reference.

There is a need for searching derivatives of the novel fused pyrazolyl compounds disclosed in U.S. Pat. No. 7,378,532 B2, which possess pharmaceutically useful properties.

SUMMARY OF THE INVENTION

An objective of the present invention is to provide novel fused pyrazolyl compounds having an aminoalkylcarbonyl group, and the use thereof in inhibiting cancer cell growth.

Another objective of the present invention is to provide a pharmaceutical composition comprising an effective amount of a novel fused pyrazolyl compound having an aminoalkylcarbonyl group.

In order to accomplish the aforesaid objectives of the present invention a fused pyrazolyl compound synthesized according to the present invention has the following formula:

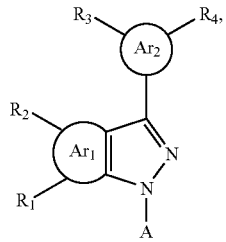

wherein A is

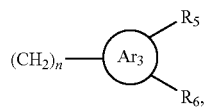

in which n is 0, 1, 2, or 3;
Ar$_1$ is benzene, thiophene or furan;
Ar$_2$ is furyl; and
Ar$_3$ is phenyl; and
R$_1$ and R$_2$ independently are hydrogen, halogen or —(CH$_2$)$_m$OR$^e$;
R$_3$ is hydrogen or alkyl;
R$_4$ is —(CH$_2$)$_r$-A$_1$, wherein r is an integer of 1-5, and A$_1$ has a formula of —O—C(O)—(CR$^c$H)$_q$—NR$^{c'}$R$^{d'}$;

R$_5$ and R$_6$ independently are hydrogen, halogen, or alkyl, or R$_5$ and R$_6$ together are —O(CH$_2$)$_m$O—;
R$^c$ is H, halogen, nitro, cyano, alkyl, or aryl;
R$^e$ is H, alkyl, or aryl;
R$^{c'}$ and R$^{d'}$ independently are H, alkyl, or aryl;
m is 0, 1, 2, 3, 4, 5, or 6; and
q is 1, 2, 3, 4, 5, or 6; or
a salt thereof.

The present invention also provide a pharmaceutical composition comprising an effective amount of the novel fused pyrazolyl compound having the above formula.

Preferably, Ar$_2$ is 2'-furyl.
Preferably, R$_3$ is H and R$_4$ is bonded to position 5 of furyl.
Preferably, R$^{c'}$ and R$^{d'}$ independently are H or alkyl. More preferably, R$^{c'}$ and R$^{d'}$ are both H.
Preferably, R$^c$ is H.
Preferably, q is 1 or 2.
Preferably, r is 1.
Preferably, Ar$_1$ is benzene.
Preferably, A is —CH$_2$-phenyl.
Preferably, the compound has the following structure:

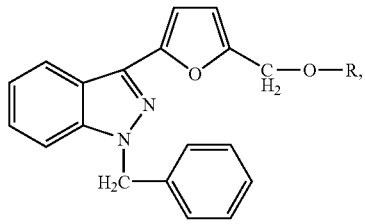

wherein R is

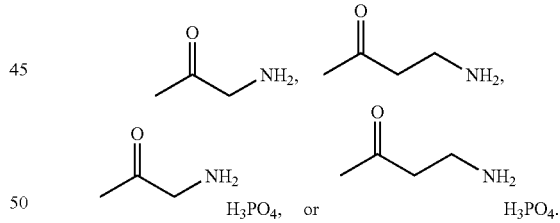

DETAILED DESCRIPTION OF THE INVENTION

Abbreviation:
Gly: Glycine
Ala: Alanine
Fmoc: 9-Fluorenylmethoxycarbonyl
HBTU: 2-(1H-Benzotriazole-1-yl)-1,1,3,3-tetramethyluronium hexafluorophosphate
DMAP: 4-(Dimethylamino)pyridine
ACN: 1,1'-Azobis-1-cyclohexanenitrile
DBU: 1,5-Diazabicyclo[5.4.0]undec-7-ene YC-1: 1-benzyl-3-(5'-hydroxymethyl-2'-furyl)indazole (synthesized in U.S. Pat. No. 7,378,532 B2, Example 1, (c))

EXAMPLE 1

Synthesis of Fmoc-Gly

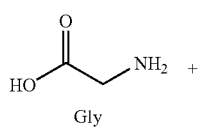

Gly

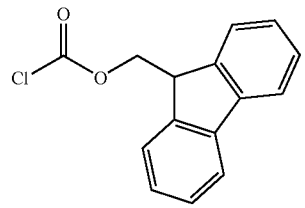

Fmoc-Cl

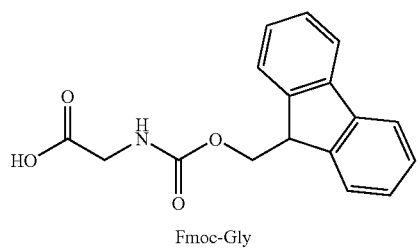

Fmoc-Gly

Glycine (Gly) (0.5 g, 6.66 mmole) was dissolved in 10% NaCO₃ (14 ml) under stirring in a 50-ml flask. To the resulting solution, which had been put into an ice bath, 9-fluorenylmethoxycarbonyl chloride (Fmoc-Cl) (1.72 g, 6.66 mmol) in dioxane (12 ml) was gradually added. The reaction mixture was stirred at room temperature for 4 hours, and water (150 ml) was then added. The aqueous phase layer was separated from the reaction mixture and stripped with ether three times (75 ml×3). The stripped aqueous layer was acidified with 2N HCl aqueous solution to a pH value of 2, followed by extraction with ethyl acetate three times (75 ml×3). The organic phase layer was recovered and concentrated to obtain crude product of 1.70 g. The crude product was recrystallized in a mixed solvent of ethyl acetate hexane=1:2 (30 ml), and white solid denoted as Fmoc-Gly was obtained after filtration at a reduced pressure. Yield: 1.69 g (85%).

NMR (CD$_3$OD) δ 3.84 (s, 2H, C$\underline{H}_2$COOH), 4.24 (t, 1H, J=7.3 Hz, Fmoc-C$\underline{H}$), 4.35 (d, 2H, J=7.0 Hz, Fmoc-C$\underline{H}_2$), 7.31 (t, 2H, J=7.0 Hz, Ar—$\underline{H}$), 7.40 (t, 2H, J=7.3 Hz, Ar—$\underline{H}$), 7.68 (d, 2H, J=7.5 Hz, Ar—$\underline{H}$), 7.80 (d, 2H, J=8.0 Hz, Ar—$\underline{H}$).

EXAMPLE 2

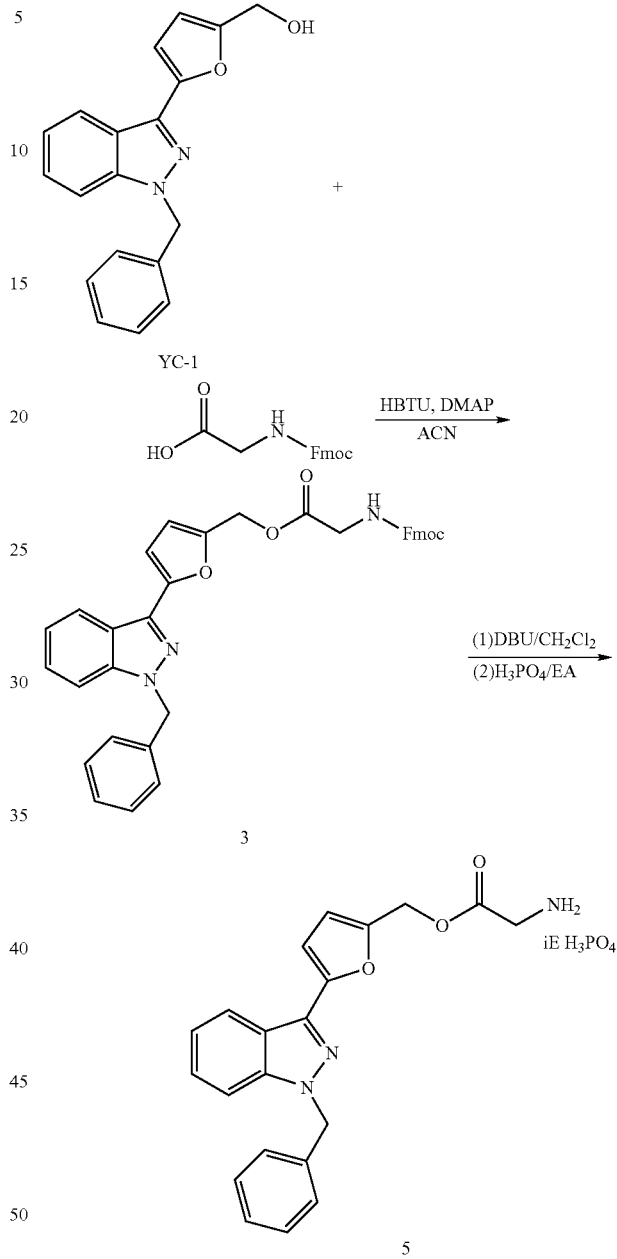

In a 50 ml flask Fmoc-Gly (488 mg, 1.64 mmole), HBTU (621 mg, 1.64 mmole), DMAP (200 mg, 1.64 mmole) and ACN (10 ml) were added and stirred until a solution was formed. To the solution YC-1 (500.0 mg, 1.64 mmole) was added and stirred at room temperature for two days. Fmoc-Gly (244 mg, 0.82 mmole), HBTU (311 mg, 0.82 mmole), DMAP (100 mg, 0.82 mmole) and ACN (10 ml) were added as supplements, and then stirred at room temperature for another three days. The reaction mixture was filtered to obtain a white crude product (1.21 g). The crude product was dissolved thoroughly in a mixed solvent of methanol: CH$_2$Cl$_2$=1:9 (10 ml), and CAN (10 ml) was added to form a precipitate. White solid 3 was obtained after filtration. Yield: 662 mg (69%).

NMR (CD$_3$OD) δ 4.04 (d, 2H, J=5.5 Hz, C$\underline{H}_2$NH), 4.21 (t, 1H, J=7.0 Hz, Fmoc-C$\underline{H}$), 4.38 (d, 2H, J=3.5 Hz, Fmoc-C$\underline{H}_2$), 5.27 (s, 2H, C$\underline{H}_2$-furan), 5.63, (s,2H, C$\underline{H}_2$-Ph), 6.59 (d, 1H, J=3.5 Hz, furan-$\underline{H}$), 6.87 (d, 1H, J=3.5 Hz, furan-$\underline{H}$), 7.18-7.38 (m,12H, Ar—$\underline{H}$), 7.57 (d, 2H, J=8.0 Hz, Ar—$\underline{H}$), 7.75 (d, 2H, J=8.0 Hz, Ar—$\underline{H}$), 8.05(d, 1H, J=8.0 Hz, Ar—$\underline{H}$)

Compound 3 (413 mg, 0.71 mmole) was dissolved in CH$_2$Cl$_2$ (10 ml) in a 50 ml flask. To the solution DBU (0.1 ml, 0.71 mmole) was added dropwise, and then stirred at room temperature for 20 minutes. Water (30 ml) was added, and the aqueous phase layer was separated and extracted with CH$_2$Cl$_2$ (30 ml). The organic phase layer was recovered and stripped with H$_2$O (50 ml). The stripped organic phase layer was concentrated and dissolved in ethyl acetate (5 ml) thoroughly. To the solution, H$_3$PO$_4$/ethyl acetate=1/10 (2 ml) was added dropwise and stirred for 30 minutes. Yellowish solid (Compound 5) was obtained after filtration at a reduced pressure.

NMR (CD$_3$OD) δ 3.88 (s, 2H, C$\underline{H}_2$NH), 5.41 (s, 2H,C$\underline{H}_2$-furan), 5.70 (s, 2H, C$\underline{H}_2$-Ph), 6.75 (d, 1H, J=3.5 Hz, furan-$\underline{H}$), 7.00 (d, 1H, J=3.5 Hz, furan-$\underline{H}$), 7.23-7.33(m,6H, Ar—$\underline{H}$), 7.46 (t, 1H, J=7.8 Hz, Ar—$\underline{H}$), 7.56 (d, 2H, J=8.5 Hz, Ar—$\underline{H}$), 8.15(d, 1H, J=8.0 Hz, Ar—$\underline{H}$)

EXAMPLE 3

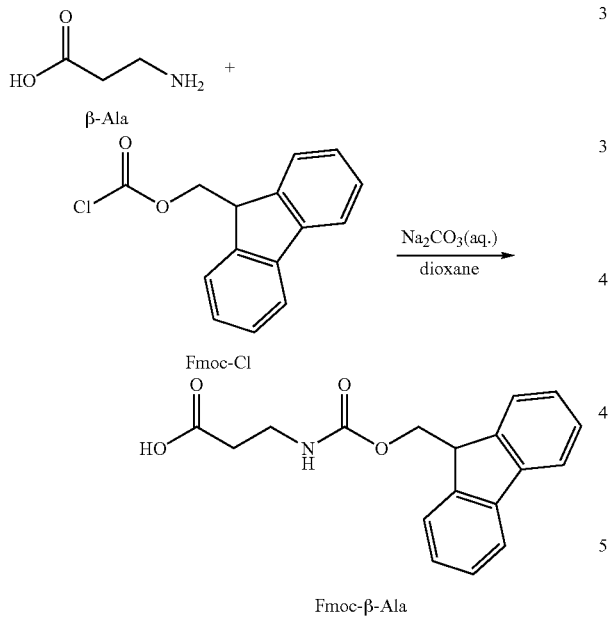

β-Alanine (β-Ala) (0.5 g, 6.61 mmole) was dissolved in 10% NaCO$_3$ (12 ml) under stirring in a 50 ml flask. To the resulting solution, which had been put into an ice bath, Fmoc-Cl (1.45 g, 5.61 mmol) in dioxane (10 ml) was gradually added. The reaction mixture was stirred at room temperature for 4 hours, and water (80 ml) was then added. The aqueous phase layer was separated from the reaction mixture and stripped with ether three times (75 ml×3). The stripped aqueous layer was acidified with 2N HCl aqueous solution to a pH value of 2, followed by extraction with ethyl acetate three times (75 ml×3). The organic phase layer was recovered and concentrated to obtain crude product of 1.50 g. The crude product was recrystallized in a mixed solvent of ethyl acetate:hexane=1:2 (30 ml), and white solid denoted as Fmoc-β-Ala was obtained after filtration at a reduced pressure. Yield: 1.41 g (81%).

NMR (CDCl$_3$) δ 2.60 (t, 2H, NHCH$_2$C$\underline{H}_2$COOH), 3.47 (d, 2H, J=7.0 Hz, NHC$\underline{H}_2$CH$_2$COOH), 4.19 (t, 1H, J=6.0 Hz, Fmoc-C$\underline{H}$), 4.39 (d, 2H, J=7.0 Hz, Fmoc-C$\underline{H}_2$), 7.29 (t, 2H, J=7.3 Hz, Ar—$\underline{H}$), 7.38 (t, 2H, J=7.3 Hz, Ar—$\underline{H}$), 7.56 (d, 2H, J=7.0 Hz, Ar—$\underline{H}$), 7.74 (d, 2H, J=7.5 Hz, Ar—$\underline{H}$).

EXAMPLE 4

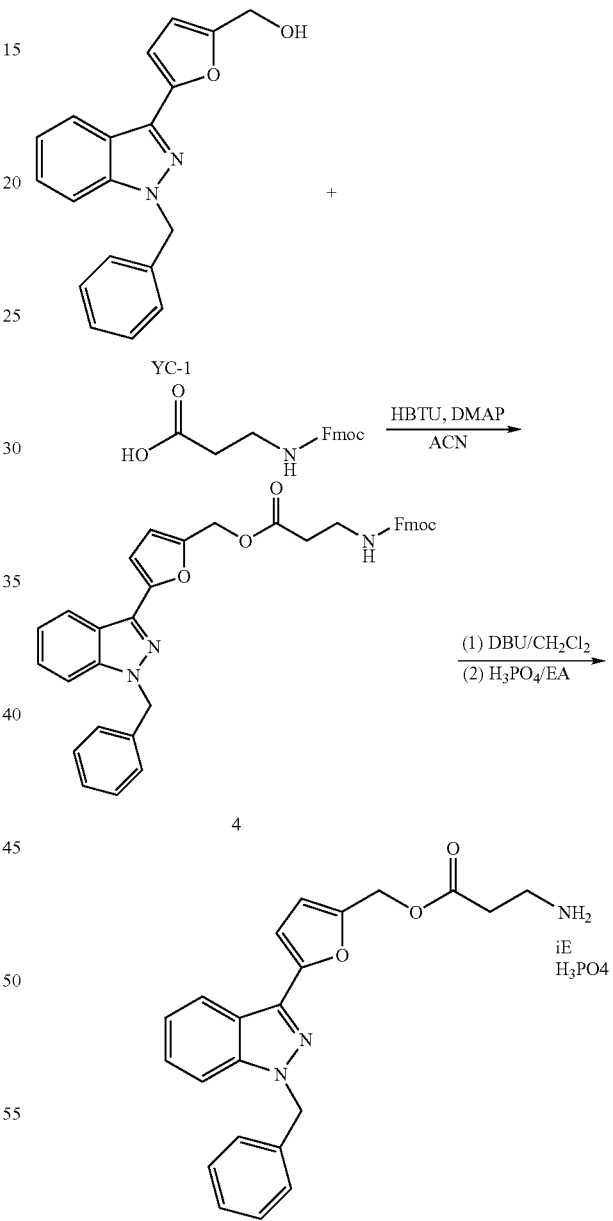

In a 50 ml flask Fmoc-β-Ala (488 mg, 1.64 mmole), HBTU (621 mg, 1.64 mmole), DMAP (200 mg, 1.64 mmole) and ACN (10 ml) were added and stirred until a solution was formed. To the solution YC-1 (500.0 mg, 1.64 mmole) was added and stirred at room temperature for two days. Fmoc- β-Ala (244 mg, 0.82 mmole), HBTU (311 mg, 0.82 mmole), DMAP (100 mg, 0.82 mmole) and ACN (10 ml) were added as supplements, and then stirred at room temperature for another three days. The reaction mixture was filtered to obtain a yellowish crude product (1.05 g). The crude product was dissolved thoroughly in a mixed solvent of methanol: $CH_2Cl_2$=1:9 (5 ml), and ACN (10 ml) was added to form a precipitate. White solid 4 was obtained after filtration. Yield: 690 mg (70%).

NMR ($CDCl_3$) δ 2.60 (t, 2H, NHCH$_2$C$\underline{H}_2$), 3.48 (d, 2H, J=2.8 Hz, NHC$\underline{H}_2$CH$_2$), 4.21 (t, 1H, J=7.0 Hz, Fmoc-C$\underline{H}$), 4.33 (d, 2H, J=3.5 Hz, Fmoc-C$\underline{H}_2$), 5.23 (s, 2H, C$\underline{H}_2$-furan), 5.61, (s,2H, C$\underline{H}_2$-Ph), 6.58 (d, 1H, J=3.0 Hz, furan-$\underline{H}$), 6.88 (d, 1H, J=3.5 Hz, furan-$\underline{H}$),7.17-7.37 (m, 12H, Ar—$\underline{H}$), 7.53 (d, 2H, J=7.5 Hz, Ar—$\underline{H}$), 7.72 (d, 2H, J=7.5 Hz, Ar—$\underline{H}$), 8.05(d, 1H, J=8.0 Hz, Ar—$\underline{H}$).

Compound 4 (363 mg, 0.61 mmole) was dissolved in $CH_2Cl_2$ (10 ml) in a 50 ml flask. To the solution DBU (0.08 ml, 0.61 mmole) was added dropwise, and then stirred at room temperature for 20 minutes. Water (30 ml) was added, and the aqueous phase layer was separated and extracted with $CH_2Cl_2$ (30 ml). The organic phase layer was recovered and stripped with $H_2O$ (50 ml). The stripped organic phase layer was concentrated and dissolved in ethyl acetate (5 ml) thoroughly. To the solution, $H_3PO_4$/ethyl acetate=1/10 (2 ml) was added dropwise and stirred for 30 minutes. Yellowish solid (Compound 6) was obtained after filtration at a reduced pressure.

NMR ($CD_3OD$) δ 2.79 (t, 2H, J=6.5 Hz, C$\underline{H}_2$CH$_2$NH), 3.20 (t, 2H, J=6.5 Hz, CH$_2$C$\underline{H}_2$NH), Ar—$\underline{H}$), 5.32 (s, 2H, C$\underline{H}_2$-furan), 5.70, (s,2H, C$\underline{H}_2$-Ph), 6.70 (d, 1H, J=3.5 Hz, furan-$\underline{H}$), 6.99 (d, 1H, J=3.0 Hz, furan-$\underline{H}$), 7.23-7.33(m,6H, Ar—$\underline{H}$), 7.46 (t, 1H, J=3.5 Hz, Ar—$\underline{H}$), 7.56 (d, 2H, J=8.5 Hz, Ar—$\underline{H}$), 8.14(d, 1H, J=8.5 Hz, Ar—$\underline{H}$).

The Cytotoxicity of Compounds Against NCI H-226 Cells

The target compound 5, 6 and related succinate (A), glutamate (B) derivatives were evaluated in a MTT assay against NCI H226 cells, and the results are shown in Table 1. All of the tested compounds exhibited significant cytotoxicity.

TABLE 1

Cytotoxicity of compounds against NCI H-226 cells

| Compound | R | Conc. (μM) | MTT % |
|---|---|---|---|
| A | (succinate, ONa) | 0.10<br>1.0<br>10.0 | 87.5 ± 2.2<br>53.1 ± 2.6<br>0 |
| B | (glutarate, ONa) | 0.10<br>1.0<br>10.0 | 99.9 ± 2.6<br>86.6 ± 3.9<br>0 |
| 5 | (—C(O)CH$_2$NH$_2$·H$_3$PO$_4$) | 0.10<br>1.0<br>10.0 | 85.8 ± 1.7<br>18.5 ± 3.9<br>0 |
| 6 | (—C(O)CH$_2$CH$_2$NH$_2$·H$_3$PO$_4$) | 0.10<br>1.0<br>10.0 | 106.8 ± 2.6<br>92.3 ± 1.5<br>0 |

NCI H-226 cells (4 × 10$^4$) were treated separately with compounds A, B, 5, and 6 for 72 hrs. After treatment, cells were harvested and examined using MTT assay.

Bioassay

Materials and Methods

1. Cell Culture and Treatment

The NCI H-226 cells were maintained in RPMI-1640 medium supplemented with 10% fetal bovine serum (GIBCO/BRL), penicillin (100 unit/mL)/streptomycin (100 μg/mL) (GIBCO/BRL) and 1% L-glutamine (GIBCO/BRL) at 37° C. in a humidified atmosphere containing 5% $CO_2$. Logarithmically growing tumor cells were used for all experiments.

2. Cytotoxicity Assay

The cytotoxicity was assessed using MTT assay.[1] NCI H-226 cells (4×10$^4$) were treated separately with compounds A, B, 5, and 6 for 72 h. After treatment, the cells were collected, washed with cold PBS, and then added 10 μL of MTT solution (5 mg/mL)(Sigma) with 50 μL of cells suspension in HBSS into 96-well plate and incubated them at 37° C. in the dark for 2 h. Treatment of living cells with MTT produces a dark blue formazan product, whereas no such staining is observed in dead cells. The formazan product was dissolved by adding 140 μL DMSO and then the absorbance was measured on an ELISA reader at a best wavelength of 570 nm.

3. Statistic Evaluation

Values are expression as the mean ±S.D. of three independent experiments. Student's t tests were used to assess the statistical significance of the differences, with "p" values of less than 0.05 being considered statistically significant.

REFERENCES AND NOTES

1. Hsu, M. H., Kuo, S. C., Chen, C. J., Chung, J. G., Lai, Y. Y., Huang, L. J. 1-(3,4-di-methoxy-phenyl)-3-,5-dodecenedione (I6) induces G1 arrest apoptosis in human promyelocytic leukemia HL-60 cells. *Leukemia Res.* 2005, 29, 1399-1406.
2. Chen C. J.; Hsu, M. H.; Kuo, S. C.; Lai, Y. Y.; Chung, J. G.; Huang, L. J. (2E)-3-(4-hydroxy-3-methoxyphenyl)acrylamide induction apoptosis and cell cycle arrest in HL-60 cells. *Anticancer Res.* 2007, 27, 343-350.

The invention claimed is:
1. A fused pyrazolyl compound having the following formula:

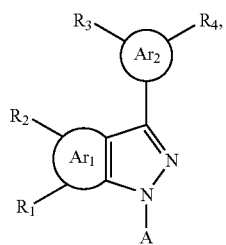

wherein A is

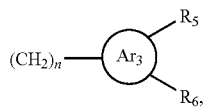

in which n is 0, 1, 2, or 3;
$Ar_1$ is benzene, thiophene or furan;
$Ar_2$ is furyl;
$Ar_3$ is phenyl;
$R_1$ and $R_2$ independently are hydrogen, halogen or —$(CH_2)_m OR^e$;
$R_3$ is hydrogen or alkyl;
$R_4$ is —$(CH_2)_r$-$A_1$, wherein r is an integer of 1-5, and $A_1$ has a formula of —O—C(O)—$(CR^cH)_q$—$NR^{c'}R^{d'}$;
$R_5$ and $R_6$ independently are hydrogen, halogen, or alkyl, or $R_5$ and $R_6$ together are —$O(CH_2)_m O$—;
$R^c$ is H, halogen, nitro, cyano, alkyl, or aryl;
$R^e$ is H, alkyl, or aryl;
$R^{c'}$ and $R^{d'}$ independently are H, alkyl, or aryl;
m is 0, 1, 2, 3, 4, 5, or 6; and
q is 1, 2, 3, 4, 5, or 6; or
a salt thereof.
2. The compound of claim 1, wherein $Ar_2$ is 2'-furyl.
3. The compound of claim 2, wherein $R_3$ is H and $R_4$ is bonded to position 5 of furyl.
4. The compound of claim 3, wherein $R^{c'}$ and $R^{d'}$ independently are H or alkyl.
5. The compound of claim 4, wherein $R^{c'}$ and $R^{d'}$ are both H.
6. The compound of claim 3, wherein $R^c$ is H.
7. The compound of claim 3, wherein q is 1 or 2.
8. The compound of claim 3, wherein r is 1.
9. The compound of claim 1, wherein $Ar_1$ is benzene.

10. The compound of claim 8, wherein A is —$CH_2$-phenyl.
11. A pharmaceutical composition comprising an effective amount of a compound of the following formula:

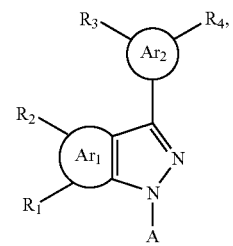

wherein A is

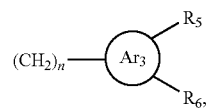

in which n is 0, 1, 2, or 3;
$Ar_1$ is benzene, thiophene or furan;
$Ar_2$ is furyl;
$Ar_3$ is phenyl;
$R_1$ and $R_2$ independently are hydrogen, halogen or —$(CH_2)_m OR^e$;
$R_3$ is hydrogen or alkyl;
$R_4$ is —$(CH_2)_r$-$A_1$, wherein r is an integer of 1-5, and $A_1$ has a formula of —O—C(O)—$(CR^cH)_q$—$NR^{c'}R^{d'}$;
$R_5$ and $R_6$ independently are hydrogen, halogen, or alkyl, or $R_5$ and $R_6$ together are —$O(CH_2)_m O$—;
$R^c$ is H, halogen, nitro, cyano, alkyl, or aryl;
$R^e$ is H, alkyl, or aryl;
$R^{c'}$ and $R^{d'}$ independently are H, alkyl, or aryl;
m is 0, 1, 2, 3, 4, 5, or 6; and
q is 1, 2, 3, 4, 5, or 6; or
a salt thereof.
12. The composition of claim 11, wherein $Ar_2$ is 2'-furyl.
13. The composition of claim 12, wherein $R_3$ is H and $R_4$ is bonded to position 5 of furyl.
14. The composition of claim 13, wherein $R^{c'}$ and $R^{d'}$ independently are H or alkyl.
15. The composition of claim 14, wherein $R^{c'}$ and $R^{d'}$ are both H.
16. The composition of claim 13, wherein $R^c$ is H.
17. The composition of claim 13, wherein q is 1 or 2.
18. The composition of claim 13, wherein r is 1.
19. The composition of claim 11, wherein $Ar_1$ is benzene.
20. The composition of claim 19, wherein A is —$CH_2$-phenyl.

21. The compound of claim 1 having the following structure:
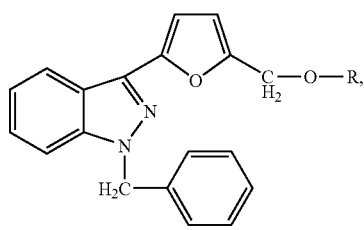
wherein R is
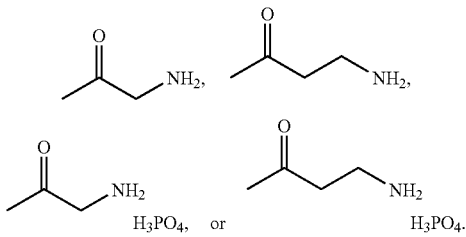
22. The composition of claim 11, wherein the compound has the following structure:
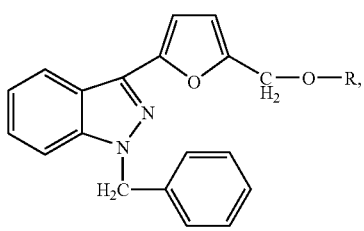
wherein R is
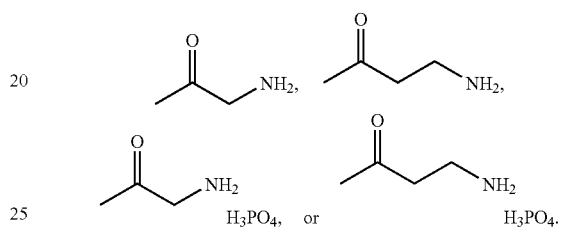
* * * * *